United States Patent [19]

Riess

[11] 4,215,986
[45] Aug. 5, 1980

[54] ARRANGEMENT FOR THE SHOCK-ABSORBENT MOUNTING AND SUPPORT OF A DENTAL SUPERSTRUCTURE

[76] Inventor: Guido Riess, Marienplatz 7, 8100 Garmisch-Partenkirchen, Fed. Rep. of Germany

[21] Appl. No.: 959,294

[22] Filed: Nov. 9, 1978

[30] Foreign Application Priority Data

Jul. 7, 1978 [DE] Fed. Rep. of Germany ....... 2830025

[51] Int. Cl.² ............................................... A61C 8/00
[52] U.S. Cl. .................................... 433/173; 433/169
[58] Field of Search ................................ 32/10 A, 13

[56] References Cited

U.S. PATENT DOCUMENTS

| | | | |
|---|---|---|---|
| 443,144 | 12/1890 | Low | 32/13 |
| 3,827,145 | 8/1976 | Richards | 32/10 A |

Primary Examiner—Robert Peshock
Attorney, Agent, or Firm—Scully, Scott, Murphy & Presser

[57] ABSTRACT

An arrangement for the shock-absorbent mounting and support of a dental superstructure, such as a tooth crown, a fastening element for dental bridges and the like, on an artificial tooth having an implantable root and an intermediate member of a tissue-compatible material facilitating a sealing contact with the gingiva, a mounting member for the dental superstructure having a detachable threaded connection interconnecting the intermediate member with the mounting member. A rockable support encompasses the threaded connection so as to form a hollow space there-about, the rockable support extending into a lip sealingly engaged along an outer edge on an upper surface of the intermediate member.

2 Claims, 2 Drawing Figures

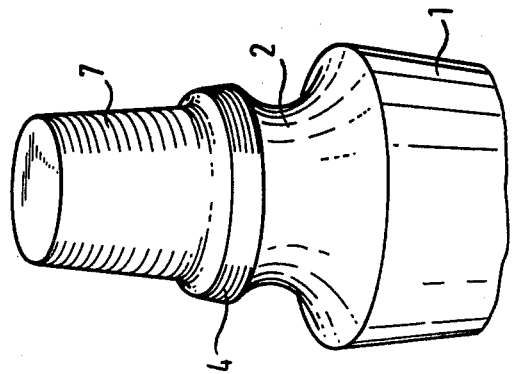
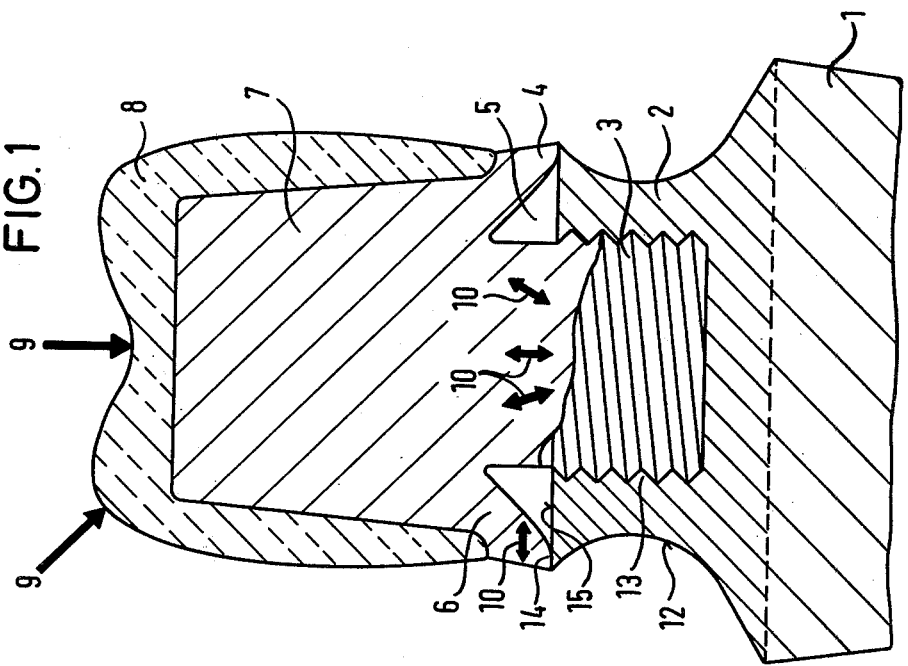

ARRANGEMENT FOR THE SHOCK-ABSORBENT MOUNTING AND SUPPORT OF A DENTAL SUPERSTRUCTURE

BACKGROUND OF THE INVENTION

1. Field of the Invention

The present invention relates to an arrangement for the shock-absorbent mounting and support of a dental super-structure, in essence, a tooth crown, a fastening element for dental bridges and the like, on an artificial tooth having an implantable root and a tissue-compatible intermediate member which provides for a close contact of the gum skin or gingiva.

2. Discussion of the Prior Art

An arrangement of this type has already been proposed in applicant's copending U.S. Pat. application No. 867,336. Therein, the implantable root is constituted of a biostable polymer matrix including embedded reabsorbable and non-reabsorbable calcium phosphate. The intermediate member of a tissue-compatible material which supports the close or sealing contact of the gingiva is connected with a core member which is embedded in the polymer matrix and is provided with a tapered surface. In this known artificial tooth the shock-absorbent connection between the super-structure and the tooth root, respectively the intermediate member, is constituted of a metal sleeve adapted to receive the superstructure, which is filled with silicon rubber or a similar resilient plastic material and into which there extends a bolt which is connected to or screwed together with the core of the tooth root.

An artificial tooth has become known from German Laid-Open Patent Application No. 2,247,649 in which a superstructure in the form of a crown is resiliently fastened on the root so as to create a hollow space between a threaded plug and the crown which is filled with an elastomeric material which permits an elastic movement of the crown within a predetermined extent during use whereby the crown is seated either resiliently or in a pillowed manner.

For implantable teeth it is necessary that the superstructure be shock-resiliently connected with the implanted root in order to maintain undesirable loads remote from the root. Thereby it is necessary that axial and diagonal shock loads acting in the most widely differing spatial directions be as uniformly as possible received and contained. In the known utilization of an elastic intermediate layer of an elastomeric material or the like, considerable difficulties are encountered in the determination of the impact elasticity with respect to the different directions of the shocks. In order to be able to absorb shocks equally well in all directions, it is necessary to employ complex shapes and constructions with regard to the inserted elastomeric materials.

SUMMARY OF THE INVENTION

Accordingly, it is an object of the present invention to provide a constructively simple, detachable shock-absorbent connecting arrangement which will be adequate without the interposition of resilient intermediate members or intermediate layers.

In order to achieve the foregoing object, there is inventively proposed in an arrangement of the above-mentioned type that there be provided a mounting member for receiving the superstructure, which is connected with the intermediate member by means of a releasable threaded connection, including a rockable support extending into a lip encompassing the threaded connection while forming a hollow space therebetween and which is sealingly supported along the edge of an upper surface on the intermediate member. The rockable support of the mounting member facilitates the shock-resilient assumption of the axial as well as of the radial and diagonal shock loads which act on the superstructure, without necessitating the mounting member itself to be constituted of a material which falls within the classification of exclusively resilient or elastic materials. The mounting member can consist of plastic material which is based on a polysulfonate, macrolons, acrylates or the like which, on the one hand, provides sufficient rigidity for the construction of the threaded connection and, on the other hand, for the fixed mounting and fastening of the superstructure. The impact elasticity between the mounting member and the intermediate member is essentially attained by only the rockable support which is sealingly supported on the upper surface of the intermediate member by means of its lip, which annularly encompasses the threaded connection so as to encompass a hollow space and leads to the desired impact elasticity through its cross-sectional configuration. Concurrently, by means of the lip there is produced a precisely shaped transition between the intermediate member and the mounting member which is sealed with respect to impurities.

In a suitable embodiment of the invention, the mounting member is provided with a central threaded projection having an external thread, which is encompassed by the rockable support and can be screwed into the internal thread of a threaded bore in the intermediate member. In a further advantageous embodiment, the rockable support is constructed so as to be approximately triangular in cross-section and the hollow space is also approximately triangular whereby, when the mounting member is attached, the one side of the hollow space is bordered by the threaded projection, the second side by the rockable support, and the third side by the upper surface of the intermediate member.

BRIEF DESCRIPTION OF THE DRAWINGS

Reference may now be had to the detailed description of an exemplary embodiment of the invention, taken in conjunction with the accompanying drawings; in which:

FIG. 1 schematically illustrates, in a sectional view, the upper portion of an artificial tooth with the inventive mounting member; and FIG. 2 is a smaller scaled perspective view of the upper portion of an artificial tooth with the inventive support member illustrated without a dental superstructure.

DETAILED DESCRIPTION

The artificial tooth is constituted of an implantable root structure 1 of suitable construction and of intermediate member 2 with a tapered surface 12 which is integral with or fastened to the root structure for rendering easier the growing on of the gum skin (gingiva). At least the intermediate member is constituted of a material which supports the sealing contact of the gingiva and, for example, consists of titanium. The threaded portion 2 includes a threaded bore 13 with internal threads into which there is detachably screwed the externally threaded projection 3 of a mounting member 7. The mounting member 7 thus has its construction form the so-called epimobile mounting for the formation of the shock-absorbent application and support of the dental superstructure. The dental superstructure is a tooth crown 8 in the illustrated embodiment of FIG. 1, which is rigidly interconnected with the mounting member 7 in a suitable manner.

The mounting member 7 includes, in cross-section, an approximately triangularly-shaped rockable support 4 which annularly encompasses the threaded projection 3, and extends into a lip 14 which, when the threaded projection 3 is screwed into the threaded bore 13, will sealingly engage the outer edge of the upper surface 15 of the intermediate member 2. In that manner, a generally triangular, annular hollow space 5 in cross-section is formed intermediate the rockable support 4 and the threaded projection 3, as well as the surface 15. This hollow space, and respectively, the configuration of the rockable support 4 permits that, essentially, in the areas of the mounting member 7 which are designated by reference numeral 6, there will be an adequate resilient deformation during shock-like loading of the superstructure 8, for instance, in the direction of the arrows 9. The elastic resilience in the areas 6 of the mounting member 7 is indicated by the arrows 10. The desired elastic resilience of the mounting member with respect to shock loads acting in predetermined directions can be set through the selection of the cross sectional shape and size of the rockable supports 4 and the threaded projection 3, as well as, partly, by the selection of the material for the mounting member.

What is claimed is:

1. In an arrangement for the shock-absorbent mounting and support of a dental superstructure, such as a tooth crown, a fastening element for dental bridges and the like, on an artificial tooth having an implantable root and an intermediate member of a tissue-compatible material facilitating a sealing contact with the gingiva, the improvement comprising: a mounting member for said dental superstructure having a central externally threaded projection; said intermediate member including an internally threaded bore engageable with said central externally threaded projection to form a detachable threaded connection interconnecting said intermediate member with said mounting member; and said intermediate member including a rockable support encompassing said threaded connection so as to form a hollow space thereabout, said rockable support extending into a lip sealingly engaged along on outer edge on an upper surface of said intermediate member, and said rockable support further being substantially triangularly shaped in cross-section and said hollow space being generally triangular in cross-section whereby, when said mounting member is fastened onto said intermediate member, said hollow space has a first side thereof bordered by the threaded projection, the second side by said rockable support, and the third side thereof by the upper surface of said intermediate member.

2. Arrangement as claimed in claim 1, said support member being unitarily formed of a plastic material selected from the group consisting of a polysulfonate, macrolon, acrylate of the like.